US00PP13051P2

(12) United States Plant Patent
Trees et al.

(10) Patent No.: US PP13,051 P2
(45) Date of Patent: Oct. 8, 2002

(54) NEW GUINEA IMPATIENS PLANT NAMED 'BALCEBPURS'

(75) Inventors: Scott Trees; Andreas Olbring, both of Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/594,173

(22) Filed: Jun. 14, 2000

(51) Int. Cl.[7] ..... A01H 5/00
(52) U.S. Cl. ..... Plt./318
(58) Field of Search ..... Plt./318

(56) References Cited

U.S. PATENT DOCUMENTS

PP11,851 P2 * 5/2001 Cosner et al. ..... Plt./318

OTHER PUBLICATIONS

UPROV–ROM GTITM Computer Database, Mar. 2001, GTI Jouve Retrieval Software, citation for 'Balcebpurs'.*

* cited by examiner

*Primary Examiner*—Bruce R. Campell
*Assistant Examiner*—Susan B. McCormick
(74) *Attorney, Agent, or Firm*—Wood, Phillips, Katz, Clark & Mortimer

(57) ABSTRACT

A new and distinct New Guinea Impatiens cultivar named 'Balcebpurs' is provided. This new cultivar was the result of a controlled irradiation program. More specifically, cuttings from 'Grape Crush' were irradiated with 2 kilorads of gamma rays and allowed to grow. One of the cuttings was discovered to exhibit a flower with petals having a distinct striping pattern and was allowed to continue to grow. The resulting plant exhibited a number of flowers having petals which exhibited the same striping pattern. This cutting/plant was designated BFP-1865.

1 Drawing Sheet

The present invention comprises a new and distinctive New Guinea Impatiens plant, hereinafter referred to by the cultivar named 'Balcebpurs'.

The new cultivar is the product of a controlled irradiation program. More specifically, cuttings from 'Grape Crush' (U.S. Plant Pat. No. 10,107) were irradiated with 2 kilorads of gamma rays and allowed to grow. One of the cuttings was discovered to exhibit a flower with petals having a distinct striping pattern and was allowed to continue growing. The resulting plant exhibited a number of flowers having petals which displayed the same striping pattern. This cutting/plant was designated BFP-1865. Asexual reproduction of the new cultivar by terminal or stem cuttings taken during 1998 and 1999 at Arroyo Grande, Calif., U.S.A. has demonstrated that the characteristics of the new cultivar as herein described are firmly fixed and are retained through successive generations of such asexual propagation.

SUMMARY OF THE INVENTION

It was found that the cultivar of the present invention:

(a) Exhibits attractive large round flowers with distinctive striping pattern, (b) Forms medium green foliage, (c) Exhibits a good basal branching character.

The 'Balcebpurs' cultivar has not been observed under all possible environmental conditions to date. Accordingly, it is possible that the phenotype may vary somewhat with variations in the environment, such as temperature, light intensity, and day length.

When the new cultivar of the present invention is compared to Grape Crush, it is found to be substantially identical in growth habit, form and size. However, the flower color is distinctly different. The flower color of the new invention exhibits a background color of Red-Purple Group 74A with stripes of Red-Purple Group 65C (adaxial) and Red-Purple Group 74B (abaxial) whereas 'Grape Crush' flowers are Red-Purple Group 74A with the lower four petals commonly displaying bases of 53C (abaxial) and Red-Purple Group 74B (abaxial).

BRIEF DESCRIPTION OF THE PHOTOGRAPH

The accompanying photographs show as nearly true as it is reasonably possible to make the same in color illustrations of this type, typical flower and foliage characteristics of the new cultivar. The plants were grown in a greenhouse at Arroyo Grande, Calif., United States of America.

DETAILED BOTANICAL DESCRIPTION

The chart used in the identification of colors described herein is The R.H.S. Colour Chart of The Royal Horticultural Society, London, England. The color values were determined on Oct. 8, 1999 in West Chicago, Ill. The readings were taken between 1:00 and 1:45 p.m. under approximately 2500 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night. The plants used for the following measurements and descriptions were grown for twelve (12) weeks from rooted cuttings.

Propagation:

*Type cutting.*—Terminal tip.

*Time to initiate roots.*—Approximately 14–21 days with the shorter times generally being experienced in the summer and the longer times in the winter.

*Rooting habit.*—Fibrous, branching.

Botanical classification: *Impatiens hawkeri.*
Commercial classification: New Guinea Impatiens.
Plant description:

*General appearance and form.*—Medium upright mounded.
*Crop time.*—A finished flowering plant is produced 10 weeks after planting rooted cuttings.
*Branching habit.*—Freely basal branching without pinching or growth regulators.
*Number of branches.*—Approximately 4.
*Branch length.*—Approximately 11.8 cm.
*Branch diameter.*—Approximately 8 mm.
*Internode length.*—Approximately 4.6 cm.
*Stem color.*—Greener than Yellow-Green Group 144A with Greyed-Purple Group 183B at nodes.
*Height of foliage.*—A mature plant commonly measures approximately 16 cm above a 10 cm pot.
*Area of spread.*—Approximately 27 cm.

Foliage description:

*Form.*—Elliptic with acuminate apex and attenuate base.
*Margin.*—Serrate ciliate.
*Arrangement.*—Alternate or in whorles of 5 or 6.
*Venation pattern.*—Arcuate.
*Surface.*—Upper surface is rough; lower surface is smooth.
*Color of mature foliage-upper surface.*—Between Green Group 137A and Green Group 143A with veins of Yellow-Green Group 148A and midrib of Greyed-Orange Group 176C.
*Color of mature foliage-lower surface.*—Between Yellow-Green Group 146B and Yellow-Green Group 147B with veins and midrib of Yellow-Green Group 148A.
*Size.*—Approximately 9.2 cm in length; approximately 3.1 cm in width.
*Petiole length.*—1.8 cm.
*Petiole diameter.*—2 mm.
*Petiole color.*—Lighter than Grey-Orange Group 176C.

Flower description:

*Flowering habit.*—'Balcebpurs' is freely flowering under outdoor growing conditions with substantially continuous blooming from spring until fall.
*Flowering borne.*—Above foliage arising from leaf axils.
*Peduncle length.*—6.1 cm.
*Peduncle color.*—146C overlaid with 183D.
*Flower form.*—Single.
*Quantity of flowers.*—Approximately 3 per lateral branch.
*Flower size.*—Approximately 5.9 cm in diameter.
*Number of petals.*—Five.
*Petal texture.*—Smooth.
*Petal shape.*—Obovate.
*Petal margin.*—Entire.
*Petal apex.*—Emarginate.
*Petal base.*—Lower petals are narrow, upper petal has broad base.
*Petal length.*—3.3 cm.
*Petal width.*—3.5 cm.
*Flower color.*—The petals are Red-Purple Group 74A with stripes of Red-Purple Group 65C (adaxial); Red-Purple Group 74B (abaxial). The petals of 'Grape Crush' are Red-Purple Group 74A with the lower four petals commonly displaying bases of Red Group 53C (adaxial); Red-Purple Group 74B (abaxial).
*Flower bud shape.*—Elliposoidal.
*Flower bud length.*—2.1 cm.
*Flower bud diameter.*—1.1 cm.
*Bud color.*—The upper surface of bud is Red-Purple 60B near the center and then gradually fades around the sides to become Red-Purple 63C at the center of the lower surface.
*Sepals.*—Three plus two rudimentary sepals fused into the under surface of the superior petal. A spur originating from the base of the inferior sepal is approximately 5.7 cm in length on fully opened flowers. The spur color is Red-Purple Group 60A with Yellow-Green Group 145A at tip. The spur of 'Grape Crush' is Red-Purple Group 74B.
*Reproductive organs.*—The anthers are fused together forming one organ that surrounds the pistil. The pistil is approximately 5 mm long, the stigma color is Yellow-Green Group 150D, the ovary color is Yellow-Green Group 144A. Generally, the anthers shed pollen to the stigma becoming receptive. The pollen color is Yellow Group 11B.
*Seed production.*—Seed production has not been observed.
*Disease resistance.*—Resistance to pathogens common to Impatiens has not been observed.

We claim:

1. A new and distinct New Guinea Impatiens plant as herein described and illustrated.

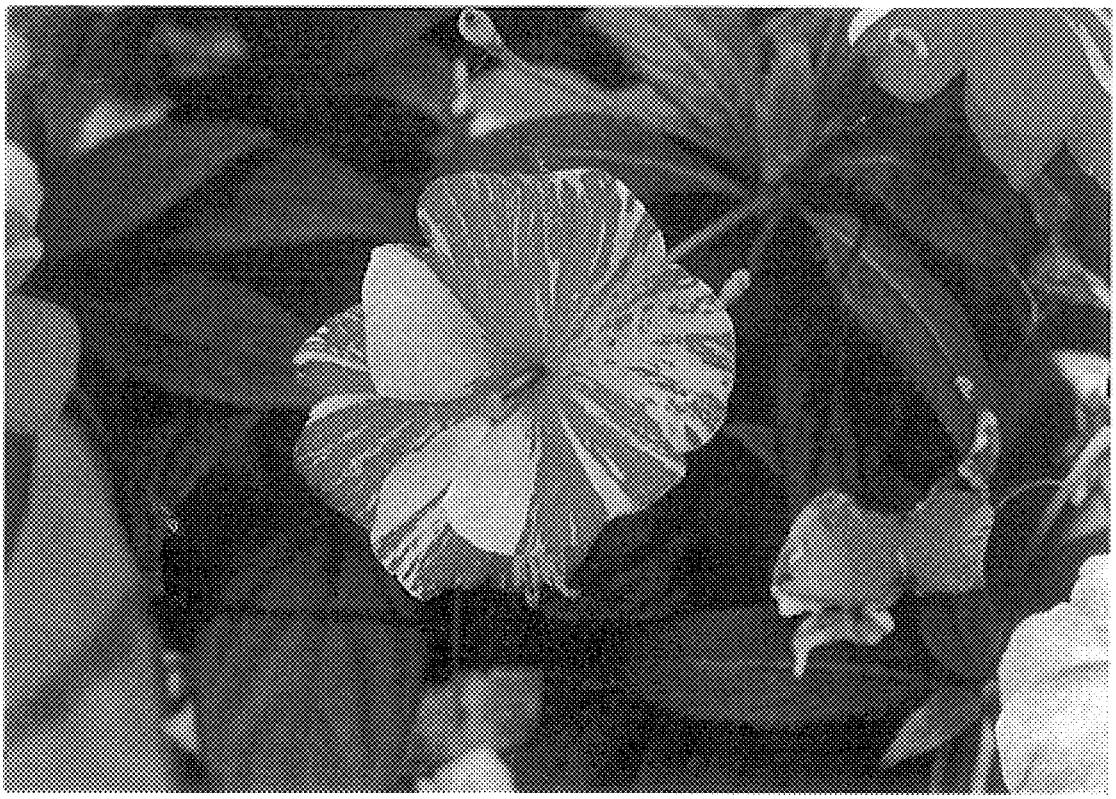

* * * * *